United States Patent [19]

Yamasaki et al.

[11] Patent Number: 5,677,420
[45] Date of Patent: Oct. 14, 1997

[54] PHOSPHOLIPASE C-INHIBITING PEPTIDES

[75] Inventors: Motoo Yamasaki; Genkichi Ishikawa, both of Machida; Yoshimi Homma, Fukushima, all of Japan

[73] Assignee: Kyowa Hakko Kogyo Co., Ltd., Tokyo, Japan

[21] Appl. No.: 737,197

[22] PCT Filed: Feb. 14, 1995

[86] PCT No.: PCT/US95/01861

§ 371 Date: Nov. 8, 1996

§ 102(e) Date: Nov. 8, 1996

[87] PCT Pub. No.: WO96/28466

PCT Pub. Date: Sep. 19, 1996

[30] Foreign Application Priority Data

Mar. 10, 1995 [JP] Japan ................................. 7-050844
Nov. 13, 1995 [JP] Japan ................................. 7-294146

[51] Int. Cl.$^6$ ................ A61K 38/00; C07K 7/00; C07K 5/00; C07K 17/00
[52] U.S. Cl. ................ 530/323; 530/328; 530/327; 530/326; 530/325
[58] Field of Search ........................ 530/323, 328, 530/327, 325, 326

[56] References Cited

U.S. PATENT DOCUMENTS 5,580,956 12/1996 Saito et al. ........................ 530/325

FOREIGN PATENT DOCUMENTS 0584374 3/1994 European Pat. Off. .
0672679 9/1995 European Pat. Off. .

OTHER PUBLICATIONS

J. Biological Chemistry, vol. 267, No. 30 (Oct. 1992) pp. 21844–21849.

J. Biological Chemistry, vol. 264, No. 36 (Dec. 1989) pp. 21885–21890.

*Primary Examiner*—Nancy Degen
*Assistant Examiner*—Matthew Latimer
*Attorney, Agent, or Firm*—Fitzpatrick, Cella, Harper & Scinto

[57] ABSTRACT

The present invention relates to phospholipase C-inhibiting peptides which are represented by formula (I):

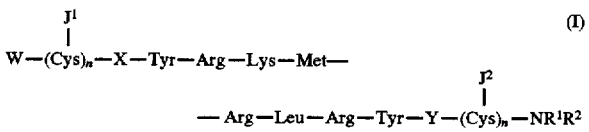

wherein n represents 0 or 1; each $J^1$ and $J^2$ is a hydrogen atom, or $J^1$ and $J^2$ are combined together to form a single bond; W represents a hydrogen atom, a substituted or unsubstituted alkanoyl group, a substituted or unsubstituted aroyl group or coumaryl group; X represents a single bond, -Leu-, or -Ser-Leu-Val-Glu-Leu-Val-Ser-Tyr-Tyr-Glu-Lys-His-Ala-Leu- (wherein at least one amino acid residue may be deleted, inserted or substituted); Y represents a single bond or -Pro-Val-; $R^1$ represents a hydrogen atom, a substituted or unsubstituted alkyl group or a substituted or unsubstituted aryl group; and $R^2$ represents a substituted or unsubstituted alkyl group or a substituted or unsubstituted aryl group.

6 Claims, No Drawings

PHOSPHOLIPASE C-INHIBITING PEPTIDES

This application is a 371 continuation of PCT/JP96/00556, filed Mar. 7, 1996, and published as WO96/28466 on Sep. 19, 1996.

TECHNICAL FIELD

The present invention relates to novel peptides which inhibit phospholipase C (hereinafter referred to as PLC) activity.

PRIOR ART

PLC, e.g., phosphatidyl inositol PLC (hereinafter referred to as PI-PLC), has been isolated and purified from various tissues in order to elucidate the mechanism of intracellular signal transduction, and the existence of nine isozymes classified into 4 types, $\alpha$, $\beta$, $\gamma$ and $\delta$ has been found so far. Type $\gamma$ is known to occur in two kinds, $\gamma_1$ and $\gamma_2$ (S.G. Rhee et al., Science, 244, 546–550, 1989; Y. Honma et al., Biochem. J., 269, 13–18, 1990), both of which have been discovered to play an important role in the signal transduction of growth factors. The structural characteristic of types $\beta$, $\gamma$ and $\delta$ is that they contain oncogene src-associated regions, SH2 and SH3 (SH2/SH3) regions between I and II regions common to $\beta$, $\gamma$ and $\delta$. The SH2 region of type $\gamma$ is essential for the interaction with receptor-type tyrosine kinase (D. Anderson et al., Science, 250, 979–982, 1990). The function of the SH3 region of type $\gamma$ is not clear, but it is supposed to be important for the interaction with the cytoskeletal system. Recently the oncogene crk which has SH2 and SH3 (SH2/SH3) regions but no kinase region was found and this has highlighted the possibility that the regulation disorders (abnormality in PI-PLC activity) and abnormal cell proliferation as mediated by the SH2 and SH3 (SH2/SH3) regions of type $\gamma$ may induce cancerous alteration. Further, there are reports which disclose that elevated PLC activity is related with pathology; for example, a report that PLC is associated with the thrombin-induced platelet activation system (J. Biol. Chem., 261, 16838–16847, 1986), a report that PLC activity is associated with histamine release (J. Cell Biol., 105, 2745–2750, 1987), a report that PLC is associated with the signal transduction pathway of the receptor for N-formylmethionyl-leucyl-phenylalanine, which is known as a substance to induce inflammation via granulocytes and polymorphonuclear leukocytes (PMN) (Science, 232, 97–100, 1986), a report that the $\beta$-chain of a platelet-derived growth factor (PDGF) is expressed in large amounts in arteriosclerotic lesions (Science, 248, 1009, 1990), reports that PLC-$\gamma_2$ exists as a constituent of the signal transduction system for the proliferation of PDGF-dependent vascular smooth muscle cells, and is closely associated with the proliferation of smooth muscle cells (Biochem. Biophys. Res. Commun., 156, 846–854, 1988, Biochem. J., 290, 649–653, 1993), and a report that PLC is increased in Alzheimer's disease (Am. J. Pathol., 139, 737–742, 1991). It is expected that these diseases can be alleviated by inhibiting PLC activity and there is a need for agents which inhibit PLC activity.

As PLC-inhibiting peptides, the following peptides are disclosed in J. Biol. Chem., 267, 21844–21849 (1992): Ser-Leu-Val-Glu-Leu-Val-Ser-Tyr-Tyr-Glu-Lys-His-Ala-Leu-Tyr-Arg-Lys-Met-Arg-Leu-Arg-Tyr-Pro-Val, Ser-Tyr-Tyr-Glu-Lys-His-Ala-Leu-Tyr-Arg-Lys-Met, Glu-Lys-His-Ala-Leu-Tyr-Arg-Lys-Met, Glu-Lys-His-Ala-Leu-Tyr-Arg-Lys-Met-Arg-Leu-Arg-Tyr-Pro-Val, Leu-Tyr-Arg-Lys-Met-Arg-Leu-Arg-Tyr-Pro-Val, Tyr-Arg-Lys-Met-Arg-Leu-Arg-Tyr, and Arg-Lys-Met-Arg-Leu-Arg.

DISCLOSURE OF THE INVENTION

The present invention provides phospholipase C-inhibiting peptides represented by formula (I):

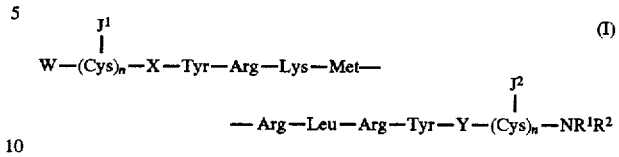

wherein n represents 0 or 1; each $J^1$ and $J^2$ is a hydrogen atom, or $J^1$ and $J^2$ are combined together to form a single bond; W represents a hydrogen atom, a substituted or unsubstituted alkanoyl group, a substituted or unsubstituted aroyl group or coumaryl group; X represents a single bond, -Leu-, or -Ser-Leu-Val-Glu-Leu-Val-Ser-Tyr-Tyr-Glu-Lys-His-Ala-Leu- (wherein at least one amino acid residue may be deleted, inserted or substituted); Y represents a single bond or -Pro-Val-; $R^1$ represents a hydrogen atom, a substituted or unsubstituted alkyl group or a substituted or unsubstituted aryl group; and $R^2$ represents a substituted or unsubstituted alkyl group or a substituted or unsubstituted aryl group.

In the definition of each group in formula (I), the alkanoyl group means an alkanoyl group having 1–20 carbon atoms, such as formyl, acetyl, propionyl, butyryl, isobutyryl, valeryl, isovaleryl, pivaloyl, hexanoyl, heptanoyl, lauroyl and icosanoyl. The substituted alkanoyl group has substituents such as carboxyl group, alicyclic alkyl group and phenyl group, and the alicyclic alkyl group means an alicyclic alkyl group having 3–8 carbon atoms, such as cyclopropyl, cyclobutyl, cyclopentyl, cyclohexyl, cycloheptyl and cyclooctyl.

The aroyl group includes benzoyl group and naphthoyl group. The substituted aroyl group has 1 to 3 substituents, such as hydroxyl group.

The alkyl group means an aklyl group having 1 to 20 carbon atoms, such as methyl, ethyl, propyl, isopropyl, butyl, pentyl, hexyl, heptyl, decyl, dodecyl and icosyl. The substituted alkyl group has substituents such as carboxyl group, carbamoyl group, alicyclic alkyl group and phenyl group, and the alicyclic alkyl group has the same meaning as defined above.

The aryl group includes phenyl group and naphthyl group. The substituted aryl group has 1 to 3 independently selected substituents, and examples of the substituents are hydroxyl group and carbamoyl group.

Hereinafter, the peptides represented by formula (I) are referred to as Compounds (I). Among Compounds (I), the peptides in which X is -Leu- and Y is -Pro-Val- are preferable. In particular, the peptides which are represented by formula (Ia):

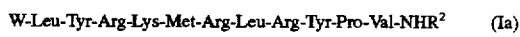

(wherein W and $R^2$ have the same meanings as defined above) are preferable. Alkanoyl group and substituted alkyl group are preferable as W and $R^2$, respectively. The peptides having the amino acid sequences shown by SEQ ID NOS: 1–9 are given as examples. The peptides having the amino acid sequences shown by SEQ ID NOS: 1–9 are referred to as Compounds (I-1)–(I-9), respectively.

The present invention is described in detail below.

The abbreviations for amino acids and their protecting groups used herein follow the recommendations by IUPAC-IUB Commission on Biochemical Nomenclature [Eur. J. Biochem., 138, 9 (1984)].

The abbreviations for amino acids and their protecting groups are as follows, unless otherwise specified.

Val: L-Valine
Leu: L-Leucine
Arg: L-Arginine
Met: L-Methionine
Lys: L-Lysine
Tyr: L-Tyrosine
Pro: L-Proline
Abu: γ-Aminobutyric acid
Ape: 5-Aminovaleric acid
Ahx: 6-Aminocaproic acid
Ahp: 7-Aminoheptanoic acid
Aoc: 8-Aminooctanoic acid
Aud: 11-Aminoundecanoic acid
Add: 12-Aminolauric acid
t-Boc: t-Butyloxycarbonyl
Fmoc: $N^\alpha$-9-Fluorenylmethoxycarbonyl The abbreviations for side-chain-protected amino acids are as follows.

Fmoc-Tyr(t-Bu)-OH: $N^\alpha$-9-fluorenylmethoxycarbonyl-O-t-butyl-L-tyrosine

Fmoc-Lys(t-Boc)-OH: $N^\alpha$-9-fluorenylmethoxycarbonyl-$N^\varepsilon$-t-butyloxycarbonyl-L-lysine Fmoc-Arg(Pmc)-OH: $N^\alpha$-9-fluorenylmethoxycarbonyl-$N^g$-2,2,5,7,8-pentamethylchroman-6-sulfonyl-L-arginine The abbreviations for reaction solvents, reaction reagents and groups are as follows.

PyBOP: Benzotriazol-1-yloxytripyrrolidino-phosphonium hexafluorophosphate
HOBt: N-Hydroxybenzotriazole
MM: N-Methylmorpholine
DMF: N,N-Dimethylformamide
TFA: Trifluoroacetic acid
Ac: Acetyl
$C_3H_7CO$: Butyryl
$CH_3(CH_2)_{16}CO$: Stearyl Compounds (I) are synthesized by a solid phase synthetic method using an automatic peptide synthesizer. A solid phase carrier resin to which a peptide is bound as obtained by the solid phase method is treated with hydrogen fluoride, TFA, etc., whereby the peptide is released from the carrier resin and at the same time the protective groups on the amino acid side chains are removed. Amidation of the C-terminal amino acids is conducted with p-methylbenzhydrylamine (BHA)-resin (Applied Biosystems, Inc., Foster City, Calif., USA; hereinafter referred to as "ABI") when a peptide synthesizer available from ABI is employed, and with Rink amide-resin or Rink amide-[4-methylbenzhydrylamine (MBHA)]-resin (Carbiochem-Novabiochem Japan, Inc.) when a peptide synthesizer available from Shimadzu Corporation is employed. Modification (acylation) of the N-terminal amino acids is conducted by removal of the N-terminal amino acid protective groups, followed by condensation using a carboxylic acid component and a condensing reagent such as PyBOP/HOBT/NMM in the same manner as in the extension of peptide chains, or by condensation using an activated carboxylic acid compound such as an acid anhydride or an acid chloride of a carboxylic acid component. The above-mentioned reactions are carried out on a synthetic resin, and after the reactions, the desired peptide derivative is obtained by cleavage from the resin. The crude product thus obtained is purified by high performance liquid chromatography (hereinafter referred to as HPLC) using a reversed-phase column to obtain a pure peptide.

Further, cyclic peptides having S—S bond can be prepared by subjecting the linear peptides obtained by the above process to air oxidation in an aqueous solution of a weak base, or to oxidation with an oxidizing agent such as potassium ferrocyanide or glutathione (oxidized form).

Examples of Compounds (I) are shown in Table 1.

TABLE 1

| Compound No. | SEQ ID NO: | Sequence |
|---|---|---|
| (I-1) | 1 | $CH_3CO$—Leu—Tyr—Arg—Lys—Met—Arg—Leu—Arg—Tyr—Pro—Val—NH—$(CH_2)_3CONH_2$ |
| (I-2) | 2 | $CH_3CO$—Leu—Tyr—Arg—Lys—Met—Arg—Leu—Arg—Tyr—Pro—Val—NH—$(CH_2)_4CONH_2$ |
| (I-3) | 3 | $CH_3CO$—Leu—Tyr—Arg—Lys—Met—Arg—Leu—Arg—Tyr—Pro—Val—NH—$(CH_2)_5CONH_2$ |
| (I-4) | 4 | $CH_3CO$—Leu—Tyr—Arg—Lys—Met—Arg—Leu—Arg—Tyr—Pro—Val—NH—$(CH_2)_6CONH_2$ |
| (I-5) | 5 | $CH_3CO$—Leu—Tyr—Arg—Lys—Met—Arg—Leu—Arg—Tyr—Pro—Val—NH—$(CH_2)_7CONH_2$ |
| (I-6) | 6 | $CH_3CO$—Leu—Tyr—Arg—Lys—Met—Arg—Leu—Arg—Tyr—Pro—Val—NH—$(CH_2)_{10}CONH_2$ |
| (I-7) | 7 | $CH_3CO$—Leu—Tyr—Arg—Lys—Met—Arg—Leu—Arg—Tyr—Pro—Val—NH—$(CH_2)_{11}CONH_2$ |
| (I-8) | 8 | $C_{17}H_{35}CO$—Leu—Tyr—Arg—Lys—Met—Arg—Leu—Arg—Tyr—Pro—Val—NH—$(CH_2)_{11}CONH_2$ |
| (I-9) | 9 | $C_3H_7CO$—Leu—Tyr—Arg—Lys—Met—Arg—Leu—Arg—Tyr—Pro—Val—NH—$(CH_2)_{11}CONH_2$ |

Compounds (I) obtained by the present invention exhibit potent PLC-inhibiting activity, cell growth-inhibiting activity and antibacterial activity.

The PLC-inhibiting activity, cell growth-inhibiting activity and antibacterial activity of Compounds (I) are illustrated in the following Experimental Examples 1, 2 and 3.

Experimental Example 1

PLC-inhibiting activity

A sample of PLC-$\gamma_1$ was prepared from bovine thymus according to the method described in Y. Honma et al., Biochem. J., 269, 13 (1990). A solution having the composition shown in Table 2 below was prepared on ice and was heated to 37° C. to start reaction. After incubation for 10 minutes, 2 ml of a chloroform/methanol mixture (2:1, v/v) was added thereto to stop the reaction. The resulting inositol phosphate was extracted with 0.5 ml of 1N hydrochloric acid. The extract was separated into two liquid phases by centrifugation (2000×g, 3 minutes), and the amount of $^3H$ contained in the supernatant (0.7 ml) was measured with a scintillation counter.

TABLE 2

| Solution | Volume (μl) |
|---|---|
| Sample (0.2 μg of purified PI-PLC-$\gamma_1$ preparation) | 10 |
| Reaction mixture | 30 |
| 1) 1M MES$^{(a)}$ NaOH buffer solution (pH 6.0) | 2.5 |
| 2) 1 mM $CaCl_2$ | 5 |
| 3) 20 mg/ml Bovine serum albumin | 2.5 |
| 4) Aqueous solution of test peptide$^{(b)}$ | 20 |
| Substrate$^{(c)}$ | 10 |

(a) 2-(N-Morpholino)ethanesulfonic acid (b) The peptides and their concentrations in aqueous solutions provided for the test are shown in Table 3.

(c) Phosphatidylinositol 4,5-bisphosphate ($PIP_2$) (500 μg), phosphatidylethanolamine (150 μg) and [$^3$H]$PIP_2$ (37 kBq) are mixed with a small amount of chloroform in advance. The lipid is dried and solidified in a nitrogen stream, and 1 ml of 0.1M KCl is added thereto, followed by ultrasonic treatment.

The inhibition rate (X) was calculated according to the following equation:

$$X\ (\%) = (A-C)/(B-C) \times 100$$

where A is the obtained value of specific radioactivity, B is the value of specific radioactivity obtained when the same amount of water was added instead of the aqueous solution of the test peptide, and C is the value of specific radioactivity obtained when the same amount of water was added instead of the sample and the aqueous solution of the test peptide.

The thus determined inhibition rates of the test peptides are shown in Table 3.

TABLE 3

| Compound | Concentration (μM) | Inhibition rate (%) |
|---|---|---|
| (I-1) | 123 | 85 |
| (I-2) | 122 | 75 |
| (I-3) | 121 | 77 |
| (I-4) | 120 | 89 |
| (I-5) | 119 | 83 |
| (I-6) | 116 | 85 |
| (1-7) | 114 | 82 |
| (I-8) | 20 | 76 |
| (I-9) | 23 | 73 |

Experimental Example 2

Cell growth-inhibiting activity

The cell growth-inhibiting activity was determined using a cell growth detection kit (Amersham) in the following manner.

KMS-4 cells [M. Nanba et al, International Journal of Cancer, 32, 697 (1983)] were suspended in DMEM medium (Nissui Pharmaceutical Co., Ltd.) containing 10% fetal calf serum at a density of 1–2×10$^4$ cells/ml, and 1 ml of the cell suspension was put into each well of a 24-well plate (Corning Inc.). The cells were cultured in a $CO_2$ incubator (37° C., 5% $CO_2$) for 2 days. Then, the medium was replaced with a fresh DMEM medium containing 10% fetal calf serum, and the test peptide was added thereto, followed by culturing for 17 hours. The medium was replaced with a serum-free DMEM medium, and 0.5 ml of a solution prepared by diluting labeled reagent 5-bromo-2'-deoxyuridine (BrdU) and 5-fluoro-2'-deoxyuridine (FdU) (10:1) 1000-fold with the same medium was added to each well, followed by culturing for 2 hours. Then the medium was removed, and the cells were immobilized with an acetic acid/ethanol solution. The immobilized cells were stained according to the method for the cell growth detection kit of Amersham, and then further stained with a 1% Giemsa solution (Merck & Co.,Inc.). The number of cells which incorporated BrdU and the total number of cells within one field of vision of a microscope (approximately 200 cells) were determined, and the proportion (%) of stained cells per field of vision was calculated. The above procedure was repeated 10 times, and the average value thereof was defined as the cell growth activity (%).

The cell growth-inhibiting activity was calculated in the following manner. That is, the cell growth inhibition rate was calculated according to the following equation:

$$X\ (\%) = (1 - B/A) \times 100$$

where A is the growth activity when no peptide was added, and B is the growth activity when the test peptide was added.

The thus determined inhibition rates of the test peptides are shown in Table 4.

TABLE 4

| Compound | Concentration (μM) | Inhibition rate (%) |
|---|---|---|
| (I-1) | 1 | 10 |
| (I-2) | 1 | 68 |
| (I-3) | 6 | 53 |
| (I-4) | 25 | 47 |
| (I-5) | 1 | 70 |
| (I-6) | 1 | 57 |
| (I-7) | 1 | 39 |

Experimental Example 3

Antibacterial activity

The minimum inhibititory concentrations (MIC) against the growth of various bacteria are shown in Table 5. The antibacterial activity was determined by the agar dilution method using a medium (pH 7.0) which comprises 3 g/l Bacto-tryptone (Difco Laboratories), 1 g/l meat extract, 1 g/l glucose and 16 g/l agar.

TABLE 5

| | MIC (μg/ml) | | | | | | | |
|---|---|---|---|---|---|---|---|---|
| Compound | PV | SS | SA | PA | EH | BS | CA | KP |
| (I-1) | 83 | — | — | 167 | — | 167 | — | — |
| (I-2) | 77 | — | — | 77 | — | 77 | — | — |
| (I-3) | 175 | — | — | 175 | — | 88 | — | — |
| (I-4) | 129 | — | — | 129 | — | 129 | — | — |
| (I-5) | — | — | — | 163 | — | 81 | — | — |
| (I-6) | 43 | — | 171 | 85 | 171 | 43 | 171 | 43 |
| (I-7) | — | — | — | 150 | — | — | — | — |
| (I-8) | 425 | 425 | 425 | 106 | 425 | 425 | — | — |
| (I-9) | 100 | — | 200 | 200 | — | 50 | — | — |

PV; *Proteus vulgaris* ATCC 6897
SS; *Shigella sonnei* ATCC 9290
SA; *Staphylococcus aureus* ATCC 6538P
PA; *Pseudomonas aeruginosa* Bin H No. 1
EH; *Enterococcus hirae* ATCC 10541
BS; *Bacillus subtilis* No. 10707
CA; *Candida albicans* ATCC 10231
KP; *Klebsiella pneumoniae* ATCC 10031

Examples of the present invention are shown below.

BEST MODE FOR CARRYING OUT THE INVENTION

The physicochemical properties shown in Examples below were determined with the following instruments.

Mass spectrometric analysis: JOEL LTD., JMS-HX110A

Amino acid analysis: Waters pico tag

In the following Examples, each peptide was synthesized with a peptide synthesizer (PSSM8, Shimadzu Corporation) according to the synthesis program of Shimadzu Corporation. Condensation reactions of the amino acids were carried out by the Fmoc method (Fundamentals and Experiments of Peptide Synthesis, Nobuo Izumiya et al., Maruzen) under standard conditions.

Protected amino acids to be used as materials are available from Shimadzu Corporation, Novabiochem, Peptide Institute Co., Ltd., Watanabe Kagaku Co., Ltd., etc.

EXAMPLE 1

Synthesis of Compound (I-1) (Ac-Leu-Tyr-Arg-Lys-Met-Arg-Leu-Arg-Tyr-Pro-Val-Abu-$NH_2$; SEQ ID NO: 1)

A carrier resin (60 mg) combined with 4-(2,4-dimethoxyphenyl-Fmoc-aminomethyl)-phenoxy was put in a reactor of an automatic synthesizer and the following treatments were carried out according to the synthesis program developed by Shimadzu Corporation.

(a) The carrier resin was washed with DMF for 3 minutes and the rinsings were discharged.

(b) To the carrier resin was added 30% piperidine-DMF solution, and the mixture was stirred for 4 minutes, followed by discharge of said solution. The same treatment was repeated.

(c) The carrier resin was washed with DMF for one minute and the rinsings were discharged. The same treatment was repeated 5 times. The carrier resin combined with $NH_2$ without Fmoc was thus obtained.

(d) DMF solution (1.05 ml) cotaining 300 μmol of Fmoc-Abu-OH, 300 μmol of PyBOP, 300 μmol of HOBt and 450 μmol of NMM was stirred for 3 minutes, and the resulting solution was added to the carrier resin. After stirring for 30 minutes, the solution was discharged.

(e) The carrier resin was washed with DMF for one minute. The same treatment was repeated 5 times to synthesize Fmoc-Abu on the carrier resin.

Subsequently, washing and deprotection steps (a)–(c) were carried out, and condensation reaction was conducted by using Fmoc-Val-OH in step (d), followed by washing step (e) to synthesize Fmoc-Val-Abu on the carrier resin. Steps (a)–(e) were repeated to obtain the carrier resin to which a protected peptide was bound. In step (d) in the repeated procedures, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys (t-Boc) -OH, Fmoc-Arg (Pmc) -OH, Fmoc-Tyr (t-Bu) -OH, and Fmoc-Leu-OH were used in turn. Then, steps (a)–(c) were carried out, and a solution obtained by stirring 1.05 ml of DMF solution containing 300 μmol of acetic anhydride for 3 minutes was added to the resin. After stirring for 30 minutes, the solution was discharged. Step (e) was conducted, and the obtained carrier resin was washed well with methanol and butyl ether, and then was dried for 2 hours under reduced pressure. To this resin was added 700 μl of a mixture of TFA, water, thioanisole, ethanedithiol, ethyl methyl sulfide, and thiophenol (82.5:5:5:2.5:3:2), and the mixture was left to stand at room temperature for 8 hours to cleave the peptide from the resin. After the resin was removed by filtration, about 15 ml of ether was added to the filtrate, and the deposited precipitate was collected to obtain a crude peptide. This crude product was purified by HPLC using a reversed-phase column (column: product of Shiseido Co., Ltd., CAPCELL PAK C18 SG120 S-5 μm30×250mm). Elution was carried out with a linear concentration gradient of acetonitrile solution containing 0.1% TFA, followed by detection at 220 nm. The obtained fraction containing Compound (I-1) was lyophilized to give 9.5 mg of Compound (I-1).

Mass spectrum : M+H=1620

Amino acid analysis: Arg 3.0 (3), Pro 0.9 (1), Tyr 2.0 (2), Val 0.7 (1), Met 0.8 (1), Leu 1.9 (2), Lys 0.9 (1) (Abu was not analyzed.)

EXAMPLE 2

Synthesis of Compound (I-2) (Ac-Leu-Tyr-Arg-Lys-Met-Arg-Leu-Arg-Tyr-Pro-Val-Ape-$NH_2$; SEQ ID NO: 2)

Condensation was carried out in the same manner as in Example 1 using 50 mg of the carrier resin combined with $NH_2$, the following N-protected amino acids: Fmoc-Ape-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and acetic anhydride. Then the peptide was cleaved from the resin and deprotected in the same manner as in Example 1 to give 36.5 mg of a crude product. The whole crude product was purified by HPLC to give 6.3 mg of Compound (I-2).

Mass spectrum : M+H=1634

Amino acid analysis: Arg 3.2 (3), Pro 0.9 (1), Tyr 2.1 (2), Val 0.6 (1), Met 0.9 (1), Leu 2.1 (2), Lys 1.1 (1 ) (Ape was not analyzed.)

EXAMPLE 3

Synthesis of Compound (I-3) (Ac-Leu-Tyr-Arg-Lys-Met-Arg-Leu-Arg-Tyr-Pro-Val-Ahx-$NH_2$; SEQ ID NO: 3)

Condensation was carried out in the same manner as in Example 1 using 50 mg of the carrier resin combined with $NH_2$, the following N-protected amino acids: Fmoc-Ahx-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and acetic anhydride. Then the peptide was cleaved from the resin and deprotected in the same manner as in Example 1 to give 40.0 mg of a crude product. The whole crude product was purified by HPLC to give 13.9 mg of Compound (I-3).

Mass spectrum : M+H=1648

Amino acid analysis: Arg 3.3 (3), Pro 1.0 (1), Tyr 2.2 (2), Val 0.6 (1), Met 0.8 (1), Leu 2.1 (2), Lys 1.0 (1) (Ahx was not analyzed.)

EXAMPLE 4

Synthesis of Compound (I-4) (Ac-Leu-Tyr-Arg-Lys-Met-Arg-Leu-Arg-Tyr-Pro-Val-Ahp-$NH_2$; SEQ ID NO: 4 )

Condensation was carried out in the same manner as in Example 1 using 50 mg of the carrier resin combined with $NH_2$, the following N-protected amino acids: Fmoc-Ahp-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and acetic anhydride. Then the peptide was cleaved from the resin and deprotected in the same manner as in Example 1 to give 20.0 mg of a crude product. The whole crude product was purified by HPLC to give 5.0 mg of Compound (I-4).

Mass spectrum : M+H=1662

Amino acid analysis: Arg 3.0 (3), Pro 1.1 (1), Tyr 2.2 (2), Val 0.6 (1), Met 0.9 (1), Leu 2.2 (2), Lys 1.0 (1) (Ahp was not analyzed.)

EXAMPLE 5

Synthesis of Compound (I-5) (Ac-Leu-Tyr-Arg-Lys-Met-Arg-Leu-Arg-Tyr-Pro-Val-Aoc-NH$_2$; SEQ ID NO: 5)

Condensation was carried out in the same manner as in Example 1 using 50 mg of the carrier resin combined with NH$_2$, the following N-protected amino acids: Fmoc-Aoc-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and acetic anhydride. Then the peptide was cleaved from the resin and deprotected in the same manner as in Example 1 to give 37.8 mg of a crude product. The whole crude product was purified by HPLC to give 10.3 mg of Compound (I-5).

Mass spectrum : M+H=1676

Amino acid analysis :Arg 3.2 (3), Pro 1.0 (1), Tyr 2.1 (2), Val 0.6 (1), Met 1.0 (1), Leu 2.1 (2), Lys 1.0 (1) (Aoc was not analyzed.)

EXAMPLE 6

Synthesis of Compound (I-6) (Ac-Leu-Tyr-Arg-Lys-Met-Arg-Leu-Arg-Tyr-Pro-Val-Aud-NH$_2$; SEQ ID NO: 6 )

Condensation was carried out in the same manner as in Example 1 using 50 mg of the carrier resin combined with NH$_2$, the following N-protected amino acids: Fmoc-Aud-OH, Fmoc-Val-OH, Fmoc-Pro-OH, Fmoc-Tyr(t-Bu)-OH, Fmoc-Arg(Pmc)-OH, Fmoc-Leu-OH, Fmoc-Arg(Pmc)-OH, Fmo-Met-OH, Fmoc-Lys(t-Boc)-OH, Fmoc-Arg(Pmc)-OH, Fmoc-Tyr(t-Bu)-OH, and Fmoc-Leu-OH, and acetic anhydride. Then the peptide was cleaved from the resin and deprotected in the same manner as in Example 1 to give 43.1 mg of a crude product. The whole crude product was purified by HPLC to give 13.1 mg of Compound (I-6).

Mass spectrum : M+H=1718

Amino acid analysis: Arg 3.2 (3), Pro 1.0 (1), Tyr 2.1 (2), Val 0.5 (1), Met 1.0 (1), Leu 2.1 (2), Lys 1.1 (1) (Aud was not analyzed.)

EXAMPLE 7

Synthesis of Compound (I-7) (Ac-Leu-Tyr-Arg-Lys-Met-Arg-Leu-Arg-Tyr-Pro-Val-Add-NH$_2$; SEQ ID NO: 7)

Condensation was carried out in the same manner as in Example 1 using 50 mg of the carrier resin combined with NH$_2$, the following N-protected amino acids: Fmoc-Add-OH, Fmoc-Val-OH, Fmoc-Pro-OH, Fmoc-Tyr (t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr (t-Bu)-OH, and Fmoc-Leu-OH, and acetic anhydride. Then the peptide was cleaved from the resin and deprotected in the same manner as in Example 1 to give 22.3 mg of a crude product. The whole crude product was purified by HPLC to give 3.9 mg of Compound (I-7).

Mass spectrum : M+H=1732

Amino acid analysis: Arg 3.3 (3), Pro 1.1 (1), Tyr 2.0 (2), Val 0.6 (1), Met 1.0 (1), Leu 2.0 (2), Lys 1.0 (1) (Add was not analyzed.)

EXAMPLE 8

Synthesis of Compound (I-8) [CH$_3$(CH$_2$)$_{16}$CO-Leu-Tyr-Arg-Lys-Met-Arg-Leu-Arg-Tyr-Pro-Val-Add-NH$_2$; SEQ ID NO: 8]

Condensation was carried out in the same manner as in Example 1 using 50 mg of the carrier resin combined with NH$_2$ , the following N-protected amino acids: Fmoc-Add-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and stearic acid. Then the peptide was cleaved from the resin and deprotected in the same manner as in Example 1 to give 45.8 mg of a crude product. The whole crude product was purified by HPLC to give 30.8 mg of Compound (I-8).

Mass spectrum : M+H=1956

Amino acid analysis: Arg 3.1 (3), Pro 1.1 (1), Tyr 2.0 (2), Val 0.5 (1), Met 1.1 (1), Leu 2.1 (2), Lys 1.0 (1) (Add was not analyzed.)

EXAMPLE 9

Synthesis of Compound (I-9) (C$_3$H$_7$CO-Leu-Tyr-Arg-Lys-Met-Arg-Leu-Arg-Tyr-Pro-Val-Add-NH$_2$; SEQ ID NO: 9)

Condensation was carried out in the same manner as in Example 1 using 50 mg of the carrier resin combined with NH$_2$, the following N-protected amino acids: Fmoc-Add-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg (Pmc)-OH, Fmoc-Tyr(t-Bu)-OH, and Fmoc-Leu-OH, and butyric anhydride. Then the peptide was cleaved from the resin and deprotected in the Same manner as in Example 1 to give 35.3 mg of a crude product. The whole crude product was purified by HPLC to give 26.4 mg of Compound (I-9).

Mass spectrum : M+H=1760

Amino acid analysis: Arg 3.1 (3), Pro 1.2 (1), Tyr 2.0 (2), Val 0.5 (1), Met 1.1 (1), Leu 2.1 (2), Lys 1.0 (1) (Add was not analyzed.)

Industrial Applicability

The present invention provides peptides which have phospholipase C-inhibiting activity.

---

We claim:

1. A phospholipase C-inhibiting peptide which is represented by formula (I):

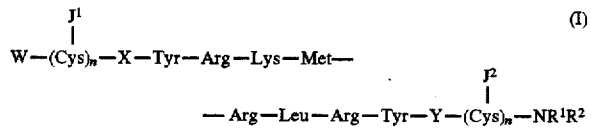
(I)

(I) wherein n represents 0 or 1; each $J^1$ and $J^2$ is a hydrogen atom, or $J^1$ and $J^2$ are combined together to form a single bond; W represents a hydrogen atom, a substituted or unsubstituted alkanoyl group, a substituted or unsubstituted aroyl group or coumaryl group; X represents a single bond, -Leu-, or -Ser-Leu-Val-Glu-Leu-Val-Ser-Tyr-Tyr-Glu-Lys-His-Ala-Leu- (wherein at least one amino acid residue may be deleted, inserted or substituted); Y represents a single bond or -Pro-Val-; $R_1$ represents a hydrogen atom, a substituted or unsubstituted alkyl group or a substituted or unsubstituted aryl group; and $R^2$ represents a substituted or unsubstituted alkyl group or a substituted or unsubstituted aryl group.

2. The peptide according to claim 1, wherein n is 0.

3. The peptide according to claim 1 or 2, wherein X is -Leu- and Y is -Pro-Val-.

4. The peptide according to claim 1 or 2, wherein $R^1$ is hydrogen.

5. A phospholipase C-inhibiting peptide which is represented by formula (Ia):

 (Ia)

wherein W represents a hydrogen atom, a substituted or unsubstituted alkanoyl group, a substituted or unsubstituted aroyl group or coumaryl group; and $R^2$ represents a substituted or unsubstituted alkyl group or a substituted or unsubstituted aryl group.

6. The peptide according to claim 3, wherein $R^1$ is hydrogen.

* * * * *

UNITED STATES PATENT AND TRADEMARK OFFICE
CERTIFICATE OF CORRECTION

PATENT NO. : 5,677,420

DATED : October 14, 1997

INVENTOR(S): MOTOO YAMASAKI ET AL.   Page 1 of 2

It is certified that error appears in the above-identified patent and that said Letters Patent is hereby corrected as shown below:

ON TITLE PAGE AT [22] PCT FILED:
  "Feb. 14, 1995" should read --March 7, 1996--.

ON TITLE PAGE AT [86] PCT NO.:
  "PCT/US95/01861" should read --PCT/JP96/00556--.

COLUMN 3
  Line 49, "MM:" should read --NMM:--.

COLUMN 6
  Table 4, "(1-3)" should read --(I-3)-- (under first column).

COLUMN 10
  Line 42, "Same" should read --same--.

UNITED STATES PATENT AND TRADEMARK OFFICE
CERTIFICATE OF CORRECTION

PATENT NO. : 5,677,420

DATED : October 14, 1997

INVENTOR(S): MOTOO YAMASAKI ET AL.

It is certified that error appears in the above-identified patent and that said Letters Patent is hereby corrected as shown below:

COLUMN 17
Line 26, "$R_1$" should read --$R^1$--.

Signed and Sealed this

Fourteenth Day of March, 2000

Attest:

Q. TODD DICKINSON

Attesting Officer     Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 12 amino acids
    ( B ) TYPE: amino acid
    ( C ) STRANDEDNESS: single (D) TOPOLOGY: linear (ii) MOLECULE TYPE: peptide (ix) FEATURE:
    (A) NAME/KEY: Modified-site
    (B) LOCATION: 1
    (C) IDENTIFICATION METHOD: by experiment
    (D) OTHER INFORMATION: /label=Xaa at location 1
        / note= "N-acetyl-L-leucine"
    (A) NAME/KEY: Modified-site
    (B) LOCATION: 12
    (C) IDENTIFICATION METHOD: by experiment
    (D) OTHER INFORMATION: /label=Xaa at location 12
        / note= "4-aminobutyramide"

(xi) SEQUENCE DESCRIPTION: SEQ ID NO:1:

```
Xaa Tyr Arg Lys Met Arg Leu Arg Tyr Pro Val Xaa
1               5                       10
```

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (C) IDENTIFICATION METHOD: by experiment
        (D) OTHER INFORMATION: /label=Xaa at location 1
            / note= "N-acetyl-L-leucine"
        (A) NAME/KEY: Modified-site
        (B) LOCATION: 12
        (C) IDENTIFICATION METHOD: by experiment
        (D) OTHER INFORMATION: /label=Xaa at location 12
            / note= "5-aminovaleramide"

(xi) SEQUENCE DESCRIPTION: SEQ ID NO:2:

```
Xaa Tyr Arg Lys Met Arg Leu Arg Tyr Pro Val Xaa
1               5                       10
```

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (C) IDENTIFICATION METHOD: by experiment
        (D) OTHER INFORMATION: /label=Xaa at location 1
            / note= "N-acetyl-L-leucine"
        (A) NAME/KEY: Modified-site
        (B) LOCATION: 12
        (C) IDENTIFICATION METHOD: by experiment
        (D) OTHER INFORMATION: /label=Xaa at location 12
            / note= "6-aminohexanamide"

(xi) SEQUENCE DESCRIPTION: SEQ ID NO:3:

```
Xaa Tyr Arg Lys Met Arg Leu Arg Tyr Pro Val Xaa
1               5                       10
```

(2) INFORMATION FOR SEQ ID NO:4:

( i ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1
   ( C ) IDENTIFICATION METHOD: by experiment
   ( D ) OTHER INFORMATION: /label=Xaa at location 1
      / note= "N-acetyl-L-leucine"
   ( A ) NAME/KEY: Modified-site
   ( B ) LOCATION: 12
   ( C ) IDENTIFICATION METHOD: by experiment
   ( D ) OTHER INFORMATION: /label=Xaa at location 12
      / note= "7-aminoheptanamide"

( x i ) SEQUENCE DESCRIPTION: SEQ ID NO:4:

Xaa Tyr Arg Lys Met Arg Leu Arg Tyr Pro Val Xaa
1               5                       10

( 2 ) INFORMATION FOR SEQ ID NO:5:

( i ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1
   ( C ) IDENTIFICATION METHOD: by experiment
   ( D ) OTHER INFORMATION: /label=Xaa at location 1
      / note= "N-acetyl-L-leucine"
   ( A ) NAME/KEY: Modified-site
   ( B ) LOCATION: 12
   ( C ) IDENTIFICATION METHOD: by experiment
   ( D ) OTHER INFORMATION: /label=Xaa at location 12
      / note= "8-aminooctanamide"

( x i ) SEQUENCE DESCRIPTION: SEQ ID NO:5:

Xaa Tyr Arg Lys Met Arg Leu Arg Tyr Pro Val Xaa
1               5                       10

( 2 ) INFORMATION FOR SEQ ID NO:6:

( i ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 1
   ( C ) IDENTIFICATION METHOD: by experiment
   ( D ) OTHER INFORMATION: /label=Xaa at location 1
      / note= "N-acetyl-L-leucine"
   ( A ) NAME/KEY: Modified-site
   ( B ) LOCATION: 12
   ( C ) IDENTIFICATION METHOD: by experiment
   ( D ) OTHER INFORMATION: /label=Xaa at location 12
      / note= "11-aminoundecanamide"

( x i ) SEQUENCE DESCRIPTION: SEQ ID NO:6:

Xaa Tyr Arg Lys Met Arg Leu Arg Tyr Pro Val Xaa
1               5                       10

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa at location 1
            / note= "N-acetyl-L-leucine"
        ( A ) NAME/KEY: Modified-site
        ( B ) LOCATION: 12
        ( C ) IDENTIFICATION METHOD: by experiment
        ( D ) OTHER INFORMATION: /label=Xaa at location 12
            / note= "12-aminododecanamide"

( x i ) SEQUENCE DESCRIPTION: SEQ ID NO:7:

```
Xaa  Tyr  Arg  Lys  Met  Arg  Leu  Arg  Tyr  Pro  Val  Xaa
 1                   5                        10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa at location 1
            / note= "N-stearoyl-L-leucine"
        ( A ) NAME/KEY: Modified-site
        ( B ) LOCATION: 12
        ( C ) IDENTIFICATION METHOD: by experiment
        ( D ) OTHER INFORMATION: /label=Xaa at location 12
            / note= "12-aminododecanamide"

( x i ) SEQUENCE DESCRIPTION: SEQ ID NO:8:

```
Xaa  Tyr  Arg  Lys  Met  Arg  Leu  Arg  Tyr  Pro  Val  Xaa
 1                   5                        10
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa at location 1
            / note= "N-butyryl-L-leucine"
        ( A ) NAME/KEY: Modified-site
        ( B ) LOCATION: 12
        ( C ) IDENTIFICATION METHOD: by experiment
        ( D ) OTHER INFORMATION: /label=Xaa at location 12
            / note= "12-aminododecanamide"

(x i) SEQUENCE DESCRIPTION: SEQ ID NO:9:

```
Xaa Tyr Arg Lys Met Arg Leu Arg Tyr Pro Val Xaa
 1           5                    10
```